(12) United States Patent
Marica et al.

(10) Patent No.: US 9,864,033 B1
(45) Date of Patent: Jan. 9, 2018

(54) FREE INDUCTION DECAY BASED MAGNETIC RESONANCE IMAGING METHODS

(71) Applicant: University of New Brunswick, Fredericton (CA)

(72) Inventors: Florea Marica, Fredericton (CA); Bruce Balcom, Fredericton (CA)

(73) Assignee: University of New Brunswick, Fredericton, New Brunswick (CA)

( * ) Notice: Subject to any disclaimer, the term of this patent is extended or adjusted under 35 U.S.C. 154(b) by 459 days.

(21) Appl. No.: 14/469,228

(22) Filed: Aug. 26, 2014

Related U.S. Application Data

(60) Provisional application No. 61/870,011, filed on Aug. 26, 2013.

(51) Int. Cl.
*G01V 3/00* (2006.01)
*G01R 33/50* (2006.01)
*G01R 33/48* (2006.01)
*G01R 33/56* (2006.01)
*G01V 3/14* (2006.01)
*G01N 24/08* (2006.01)

(52) U.S. Cl.
CPC .......... *G01R 33/50* (2013.01); *G01N 24/081* (2013.01); *G01R 33/4816* (2013.01); *G01R 33/56* (2013.01); *G01V 3/14* (2013.01)

(58) Field of Classification Search
USPC ....................................................... 324/309
See application file for complete search history.

(56) References Cited

U.S. PATENT DOCUMENTS

| | | | | | |
|---|---|---|---|---|---|
| 4,516,075 | A | * | 5/1985 | Moran | A61B 5/055 324/306 |
| 4,654,593 | A | * | 3/1987 | Ackerman | G01R 33/485 324/307 |
| 4,684,891 | A | * | 8/1987 | Feinberg | G01R 33/561 324/307 |
| 4,709,211 | A | * | 11/1987 | Machida | G01R 33/56518 324/309 |

(Continued)

OTHER PUBLICATIONS

Q. Chen, A.E. Marble, B.G. Colpitts, B.J. Balcom, "The internal magnetic field distribution, and single exponential magnetic resonance free induction decay in rocks", Journal of Magnetic Resonance 175 (2005) 300-308.

(Continued)

*Primary Examiner* — Rodney Fuller
(74) *Attorney, Agent, or Firm* — Eugene F. Derényi; Fogler, Rubinoff LLP

(57) ABSTRACT

A pure phase encode measurement method where the FID signal is encoded by a brief pure phase encode magnetic field gradient pulse. Data collection occurs once the gradient is turned off. Multiple free induction decay points acquired are identically encoded such that a full k space data set is acquired for each FID point. Fourier transformation of these data sets generates one, two or three dimensional images with consistent fields of view. The image series which results may be fit to a $T_2^*$ decay function and the $T_2^*$ magnetic resonance ("MR") lifetime mapped. Fluid content (proton density) images may also be generated by this simple fitting procedure.

12 Claims, 6 Drawing Sheets

(56) References Cited

U.S. PATENT DOCUMENTS

| | | | | |
|---|---|---|---|---|
| RE32,701 | E | * | 6/1988 | Moran ............ G01R 33/56308 324/306 |
| 5,121,059 | A | * | 6/1992 | Wieland ............ G01R 33/4828 324/307 |
| 5,122,748 | A | * | 6/1992 | Oh et al. ............ G01R 33/4833 324/307 |
| 7,230,424 | B1 | * | 6/2007 | Morrone ............ G01R 33/4835 324/309 |
| 2008/0150525 | A1 | * | 6/2008 | Song ............ G01N 24/08 324/307 |
| 2011/0249881 | A1 | * | 10/2011 | Ootsuka ............ G01R 33/56572 382/131 |
| 2012/0074938 | A1 | * | 3/2012 | Grodzki ............ G01R 33/4824 324/309 |
| 2012/0076383 | A1 | * | 3/2012 | Grodzki ............ G01R 33/4816 382/131 |
| 2013/0076357 | A1 | * | 3/2013 | Grodzki ............ A61B 5/062 324/309 |
| 2014/0232400 | A1 | * | 8/2014 | Kim ............ G01N 24/08 324/309 |

OTHER PUBLICATIONS

F. Marica, Q. Chen, A. Hamilton, C. Hall, T. Ai, B.J. Balcom, "Spatially resolved measurement of rock core porosity", Journal of Magnetic Resonance 178 (2006) 136-141.

B.J. Balcom, J.C. Barrita, C. Choi, S.D. Beyea, D.J. Goodyear, T.W. Bremner, "Single-point magnetic resonance imaging (MRI) of cement based materials", Materials Structures 36 (2003) 166-182.

R.L. Kleinberg, W.E. Kenyon, P.P. Mitra, "Mechanism of NMR relaxation of fluids in rock", Journal of Magnetic Resonance A108 (1994) 206-214.

B.J. Balcom, R.P. MacGregor, S.D. Beyea, D.P. Green, R.L. Armstrong, T.W. Bremner, "Single point ramped imaging with T1 enhancement"(SPRITE), Journal of Magnetic Resonance A123 (1996) 131-134.

S. Gravina, D.G. Cory, "Sensitivity and resolution of constant-time imaging", Journal of Magnetic Resonance B104 (1994) 53-61.

M. Halse, J. Rioux, S. Romanzetti, J. Kaffanke, B. MacMillan, I. Mastikhin, N.J. Shah, E. Aubanel, B.J. Balcom, "Centric scan SPRITE magnetic resonance imaging: optimization of SNR, resolution and relaxation time mapping", Journal of Magnetic Resonance 169 (2004) 102-117.

Z.H. Cho, Y.M. Ro, "Multipoint K-space point mapping (KPM) technique for NMR microscopy", Magn. Reson. Med. 32 (2) (1994) 258-262.

S. Emid, J. Creyghton, "High resolution NMR imaging in solids", Physica 128B (1985) 81-83.

S. Choi, X.-W. Tang, D.G. Cory, "Constant time imaging approaches to NMR microscopy", Department of Nuclear Engineering, Massachusetts Institute of Technology, vol. 8 (3) (1997) 263-276.

I.V. Mastikhin, H. Mullally, B. MacMillan, B.J. Balcom, "Water content profiles with a 1D centric SPRITE acquisition", Journal of Magnetic Resonance 156 (2002) 122-130.

M. Halse, D.J. Goodyear, B. MacMillan, P. Szomolanyi, D. Matheson, B.J. Balcom, "Centric scan SPRITE magnetic resonance imaging", Journal of Magnetic Resonance 165 (2003) 219-229.

K. Deka, M.B. MacMillan, A.V. Ouriadov, I.V. Mastikhin, J.J. Young, P.M. Glover, G.R. Ziegler, B.J. Balcom, "Quantitative density profiling with pure phase encoding and a dedicated 1D gradient", Journal of Magnetic Resonance 178 (2006) 25-32.

F.G. Goora, B. Colpitts, B.J. Balcom, "Arbitrary magnetic field gradient waveform correction using an impulse response based pre-equalization technique", Journal of Magnetic Resonance 238 (2014) 70-76.

H. Han, R.P. MacGregor, B.J. Balcom, "Pure phase encode magnetic field gradient monitor", Journal of Magnetic Resonance 201 (2009) 212-217.

K. Romanenko, B.J. Balcom, "Permeability mapping in naturally heterogeneous sandstone cores by magnetization prepared centric"—scan SPRITE, AIChE Journal, vol. 58, No. 12 ( Dec. 2012) 3916-3926.

C.E. Muir, B.J. Balcom, "Pure Phase Encode Magnetic Resonance Imaging of Fluids in Porous Media", in: G. Webb (Ed.), Annual Reports on NMR Spectroscopy, vol. 77, Academic Press, Burlington, 2012, pp. 81-113.

B.J. Balcom, M. Bogdan, R.L. Armstrong, "Single point imaging of gradient rise, stabilization, and decay", Journal of Magnetic Resonance A 118 (1996) 122-125.

* cited by examiner

FREE INDUCTION DECAY BASED MAGNETIC RESONANCE IMAGING METHODS

CROSS-REFERENCE TO RELATED APPLICATIONS

This application claims the benefit of U.S. provisional patent application No. 61/870,011 filed on Aug. 26, 2013.

TECHNICAL FIELD

The present invention relates generally to the field of magnetic resonance imaging ("MRI"), and more specifically, to the field of free induction decay ("FID") based MRI and associated methods.

BACKGROUND

There is considerable interest in fluid density imaging of a wide variety of porous media, but the difficulty in acquiring a reliable density image with no relaxation time contrast is well known. Free induction decay ("FID") based MRI methods appear to be ideally suitable to fluid content imaging, since the effective spin-spin relaxation time $T_2^*$ is frequently well behaved, and single exponential, for realistic porous media.

Experiments on sedimentary rocks [1], [2] and on typical mortar and concrete samples [3] show that the FID rate $$\left(\frac{1}{T_2^*}\right)$$

is dominated by the susceptibility difference between the pore fluid and solid matrix of the porous media sample, resulting in an effective single exponential $T_2^*$ decay, that scales with $B_0$. This occurs even when $T_2$ (the spin-spin relaxation time) and $T_1$ (the spin-lattice relaxation time) are multi-exponential due to the distribution of pore sizes [4].

Single point imaging ("SPI") uses a pulse sequence first introduced by Emid and Creyghton [9] and extensively analyzed by Choi et al. [10]. SPI and SPRITE [5], an advanced SPI method, are FID based MRI methods which have proven to be ideal for imaging short relaxation time systems. The images acquired employing SPI methods are not distorted by artifacts due to $B_0$ inhomogeneity, chemical shift and susceptibility variations [6]. The significant disadvantage is a long acquisition time, due to low flip angle RF pulses and the very limited number of FID points acquired after each excitation pulse [7]. Several modifications of SPI, focused on acquisition time reduction, have been published, including so called "multipoint k-space mapping" proposed by Cho and Ro [8]. However, with prior art FID based MRI methods, only a single data point is acquired in the presence of the gradient.

SUMMARY

In one embodiment, the present invention relates to a pure phase encode measurement method where the FID signal is encoded by a brief pure phase encode magnetic field gradient pulse. Data collection occurs once the gradient is turned off. Multiple free induction decay points are then acquired which are identically encoded such that a full k space data set is acquired for each FID point. Fourier transformation of these data sets generates one dimensional images with identical fields of view. The image series which results may be fit to a $T_2^*$ decay function and the $T_2^*$ magnetic resonance ("MR") lifetime mapped. Fluid content (proton density) images may also be generated by this simple fitting procedure. Mapping multiple FID points results in more accurate fluid content images when pore fluid is being imaged in a solid matrix.

Methods according to the present invention may be employed with 90 degree RF excitation pulses or low flip angle RF excitation. K space may be scanned in a centric manner, k space origin data acquired first, or in a sequential linear fashion. This is determined by the order of the phase encode gradient amplitudes applied. One dimensional profile imaging may be acquired and may be extended to two and three spatial dimensions in the same manner as for conventional FID based MRI methods.

According to certain aspects (but not all) of the present invention, there is provided a one dimensional ("1-D") phase-encoding sequence for $T_2^*$ mapping, for imaging a porous medium and for providing fluid content distribution in porous media. Extension to higher dimensionality imaging is straightforward. The phase-encoding sequence results in a series of individual $T_2^*$ weighted images, acquired following a RF excitation and a pulsed phase-encoding gradient. Key to the performance of methods according to embodiments of the present invention (sometimes referred to herein as "FID-SPI", is high quality control of the magnetic field gradient pulse to ensure each FID point has identical spatial encoding. FID-SPI is intended for a quantitative determination of the spatially resolved fluid content in heterogeneous porous media, having the ability to determine the $T_2^*$ decay for each image pixel. $T_2^*$ mapping aids in estimation of the local fluid content.

FID based MRI methods of the present invention may be used for a variety of purposes including proton density imaging and $T_2^*$ of physical systems. Such physical systems include, without limitation, solid matrices, including porous media such as subterranean formations, reservoir rock, sedimentary rock, mortar and concrete and wherein the porous media may contain a fluid such as water and/or a hydrocarbon, and other physical and biological systems with short $T_2$.

According to certain aspects (but not all) of the present invention, there is provided a method of MRI including providing a sample space, providing a sample in the sample space, applying a static magnetic field to the sample space, applying an RF pulse to the sample space, applying a gradient magnetic pulse to the static field, and measuring a FID signal of the sample space after the RF and gradient magnetic pulses have ceased. The RF pulse may be a 90 degree pulse or a low flip angle RF pulse. The FID signal is sampled at a series of times separated by a dwell time. The step of applying an RF pulse to the sample space may be repeated along with the step of applying a gradient magnetic pulse to the static field wherein the strength of the gradient magnetic pulse is increased or decreased (and may be increased or decreased in a series of increments) relative to the previously applied gradient pulse sequence. The gradient magnetic pulse encodes the FID signal in one, two or three directions and may further include applying a Fourier transform to generate a plurality of images, one image at each dwell time on the FID. The FID signal may be used to generate an image of the content of the pores comprising fitting a specified image pixel as a function of dwell time to yield a local value of a time constant (such as $T_2^*$) describing the local FID decay. The zero time intercept is proportional to fluid content in a porous media.

According to certain aspects (but not all) of the present invention, there is provided a method of MRI including providing a sample space, providing a sample in the sample space, applying a static magnetic field to the sample space, applying an RF pulse to the sample space, applying a phase-encode magnetic field gradient pulse to the static field thereby providing spatial encoding, measuring a FID signal of the sample space after the RF and magnetic field gradient pulses have ceased, repeating the steps of: applying an RF pulse, applying a phase-encode magnetic field gradient pulse and measuring a FID signal of the sample, wherein the step of applying a phase-encode magnetic field gradient pulse, when repeated, further comprises incrementally increasing or decreasing the phase-encode magnetic field gradient pulse relative to the last applied phase-encode magnetic field gradient pulse, and deriving an image of the sample from the FID signal measurements comprising applying a Fourier transform to generate a plurality of images, one image at each dwell time on the FID. Each RF pulse may be a 90 degree pulse or a low flip angle RF pulse. The FID signals may be a series of times separated by a dwell time. The repeated steps may be repeated a sufficient number of times in order to derive an image of interest of the sample. The method may further include providing simultaneously two orthogonal magnetic field gradient pulses and wherein the image derived from the sample is a 2-D image. The method may further include providing simultaneously three orthogonal magnetic field gradient pulses and wherein the plurality of images derived from the sample is a 3-D image. The magnetic field gradient pulses may have durations which are as short as possible such that the plurality of images have consistent FOVs. The plurality of images may be used to generate an image of proton density comprising fitting a specified image pixel as a function of dwell time to yield a local value of a time constant describing the local FID decay. The time constant may correspond to a bi-exponential decay, an exponential decay, or a non-exponential decay.

DRAWINGS

The invention is described below in greater detail with reference to the accompanying drawings which illustrate embodiments of the invention, and wherein.

DETAILED DESCRIPTION

The present invention will now be described more fully hereinafter with reference to the accompanying drawings, which are intended to be read in conjunction with the summary, the detailed description, the drawings and any preferred and/or particular embodiments specifically discussed or otherwise disclosed. This invention may, however, be embodied in many different forms and should not be construed as limited to the embodiments set forth herein. Instead, these embodiments are provided by way of illustration only and so that this disclosure will be thorough, complete and will fully convey the full scope of the invention to those skilled in the art.

The present invention relates to a FID based MRI method including a FID pulse sequence. In one or more embodiments, the FID pulse sequence of the present invention is an improved SPI pulse sequence wherein, a full spatially encoded FID is acquired after RF pulse excitation, and after the phase-encoding gradient pulse is turned off. Each FID point, appropriately phase encoded, yields a 1D image (profile) upon Fourier transformation. By having all the profiles corresponding to all the FID data points acquired, one can easily calculate the 1-D $T_2^*$ distribution map and the spin density through back extrapolation to time zero. Fitting is most readily undertaken employing a single exponential function, although the temporal resolution of the experiment would permit fitting to more complicated decay functions. A high quality, rapidly switched, shaped magnetic field gradient pulse is required to ensure spatial encoding is the same for all FID points. In one embodiment, a shaped gradient waveform that delivers a trapezoidal gradient pulse to the sample volume with gradient rise and fall times, in the sample space, of less than 200 microseconds may be used. This 1-D imaging sequence can be easily modified for acquiring 2-D and 3-D FID-SPI $T_2^*$ weighted images.

Figure 1:
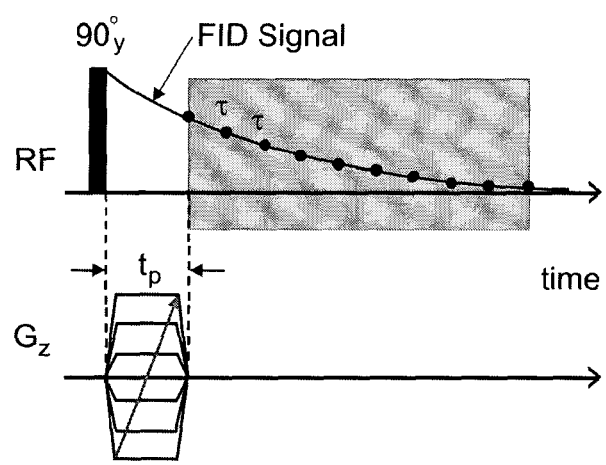
FIG. 1 is a depiction of a sequential FID pulse sequence according to an embodiment of the present invention.

A 1-D FID pulse sequence according to an embodiment of the present invention is depicted in FIG. 1, and may be used to generate a one-dimensional image for each of the acquired complex data points during the FID of the spin system. In FIG. 1, the phase encoding gradient $G_z$, applied for the encoding time $t_p$, is stepped with a 90° RF pulse applied prior to each of the magnetic field gradient amplitudes employed during the measurement, as illustrated in FIG. 1. The gray rectangle indicates the acquisition time window for the measurement.

Figure 2:
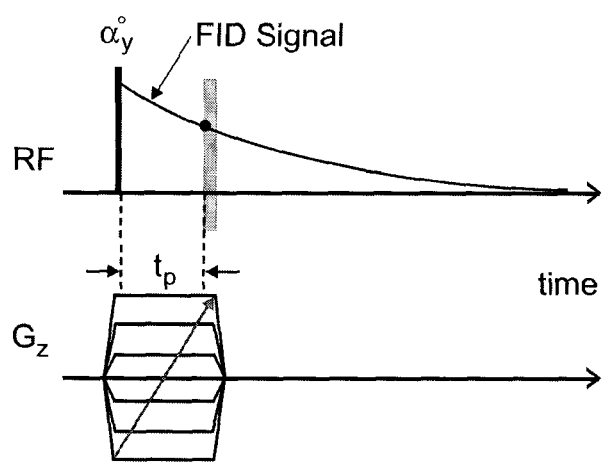
FIG. 2 is a depiction of a prior art SPI pulse sequence.

There is a discrete difference between the 1-D FID pulse sequence depicted in FIG. 1 and a conventional SPI pulse sequence. In a conventional SPI pulse sequence, such as depicted in FIG. 2, the RF pulse of angle $\propto$ is applied while the encoding gradient is on, its duration $t_\propto$ must be short enough that it covers the entire distribution of frequencies generated by the gradient, i.e.

$$t_\propto \leq 2 \cdot \frac{t_p}{n},$$

where n is the resolution [6]. In FID for the 1-D pulse sequence depicted in FIG. 1, there is no such limitation and reasonable broadband pulse widths (for example tens of microseconds for a 90° pulse excite a wider range of frequencies than the natural linewidths $$\left(\frac{1}{\pi T_2^*}\right).$$

After a 90° RF pulse and a phase-encoding gradient pulse of fixed duration $t_p$, the free induction decay (FID) signal is observed not only at a singular fixed time, as in a conventional SPI pulse sequence, but at a series of fixed times, separated by the dwell time τ. The pulse sequence is applied repeatedly and each time the strength of the magnetic field gradient pulse is incremented. A series of 1-D, $T_2^*$-weighted profiles result after Fourier transformation of the acquired data set.

The signal amplitude variations of the acquired k-space points correspond both to the $T_2^*$ decay and the phase accumulated as a function of the systematically increasing phase-encoding gradient for the duration of the encoding time $t_p$. A certain region ($z_0$) generates an NMR signal given by:

$$s(t, z_0) = S(0, z_0) \cdot \exp\left(-\frac{t}{T_2^*}\right) \cdot \exp\left(i\gamma z_0 \int_0^{t_p} G(z_0, t)dt\right) \quad (1)$$

The signal amplitude variations of the acquired phase encoding in the direction of interest (z, in FIG. 1 where is z shown in FIG. 1) is achieved by applying a gradient pulse for time $t_p$. As the resolution in phase encoding imaging depends on the gradient pulse "area" $\int_0^{t_p} G_{max(t)} dt$, where $G_{max(t)}$ is the gradient waveform for the largest gradient strength needed, for all the $T_2^*$-weighted profiles, the resolution is the same, regardless of the shape of the gradient pulses.

Figure 3:
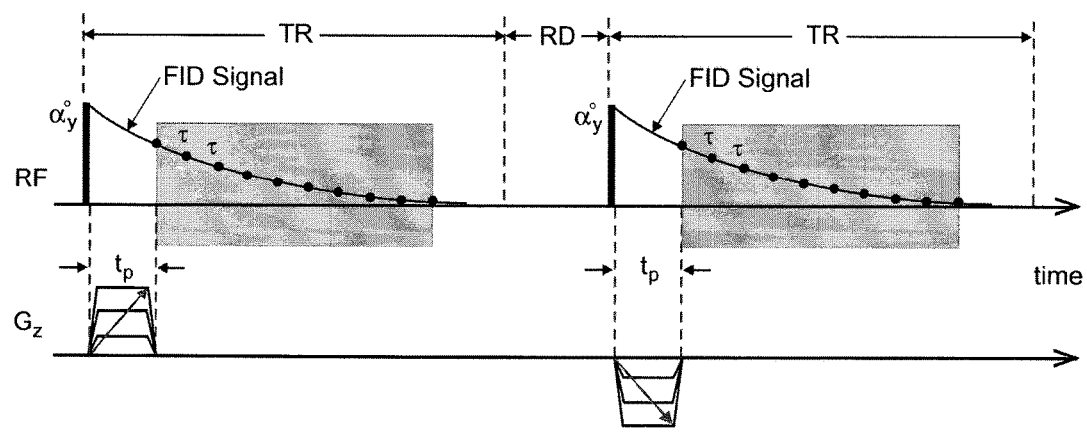
FIG. 3 is a depiction of a centric scan FID pulse sequence according to an embodiment of the present invention.

In another embodiment of the present invention, a centric scan version of a FID pulse sequence is depicted in FIG. 3. A set of FID points is acquired after a low flip angle RF pulse, $\alpha$. The phase encoding gradient $G_z$ is stepped with an RF pulse at every gradient amplitude. The encoding time is $t_p$, RD is the relaxation delay and the repetition time, TR, is the time between subsequent RF pulses. The gray rectangles in FIG. 3 indicate the acquisition time windows for each half of the k-space line. The centric scan idea was successfully integrated in the SPRITE imaging technique [11], [12], [13]. For each of the two halves of the k-space line (for 1-D), or for each of the k-space spirals (for 2-D), or for each of the k-space cones (for 3-D), the acquisition starts by sampling the k=0 point first. The RF pulse repetition time is TR and the delay RD between the k-space halves is set to be 2-5 times the longest $T_1$ of the sample, so that the centre of k-space is acquired when the longitudinal magnetization has equilibrium value $M_0$. By sampling the k-space origin first (when the gradient is off), there is no $T_1$ weighting at k=0 and hence no $T_1$ weighting in the resultant image [11]. $T_1$ instead manifests itself as a blurring factor.

It is important to rapidly (preferably less than 200 micro seconds) switch gradients and also have the gradient truly zero after the encoding time $t_p$, such that subsequent FID point derived images have identical fields of view. A recently developed pre-equalization technique [14], may be employed to calculate an input gradient waveform that yields a desired output gradient waveform, based on measurements of the system impulse response.

Experimental Examples

The Berea sandstone core plug under test was saturated with 1% (w/w) solution of NaCl in distilled water. Natural drying during the experiment was minimized by wrapping the core with Teflon tape and a plastic film. The Berea sandstone (Kokurek Industries, Caldwell, Tex.) core plug is a coarse-grained, quasi-homogeneous sandstone, considered a standard porous medium for laboratory experiments.

The local image intensity was calibrated with an external reference (a solution of 37.2% (w/w) $H_2O$, 62.1% (w/w) $D_2O$ and 0.7% (w/w) $MnSO_4.H_2O$), simulating 40% porosity. After doping, the reference $T_1$ was 1.83 ms and $T_2^*$=745 μs at 8.52 MHz.

For the brine-saturated Berea sandstone, the bulk $T_1$ measurement gave 252 ms (73%) and 36 ms (27%), when fit to a bi-exponential recovery model. The results presented here were acquired with shaped gradient pulses generated with a recently developed pre-equalization technique [14]. The first profile was acquired 250 μs after the RF pulse.

1-D, 2-D and 3-D FID pulse sequences according to embodiments of the present invention were implemented on a 3-D 8.52 MHz Maran DRX-HF imaging system (Oxford Instruments, Abingdon, UK), equipped with a 1000-watt RF amplifier (Tomco Technologies, Stepney, Australia), AE Techron 7782 gradient amplifiers (AE Techron, Elkhart, Ind.) and water cooled gradients (for the chosen direction, the maximum gradient strength was 24 G/cm). The 44 mm inner diameter home-made RF probe provided 90° RF pulses with a duration of 10.9 μs for an input RF power of 300 watts. The phase cycle, for all FID-SPI experiments was set x, y, −x, −y for the RF pulse and the same for the receiver. For the chosen UltraSpeed filter width of 125 kHz (dwell time 8 μs), the filter dead time was 19.2 μs.

The image reconstruction and data fitting were performed using various packages developed in the IDL programming environment (Exelis, Boulder, Colo.) and the final images were generated in SigmaPlot (Systat Software, San Jose, Calif.). Prior to Fourier transformation, the k-space data was smoothed with a Hanning low pass k-space filter.

Two sets of experiments were undertaken. In the first set, the 1-D FID pulse sequence of FIG. 1 was employed. The 64-pixel primary data with a field of view of 96 mm had a nominal resolution of 1.5 mm/pixel and a total of 64 profiles were acquired, separated by t of 50 μs. With an encoding time $t_p$ of 250 μs, the first profile was acquired 250 μs after the RF pulse. The highest magnetic field gradient was 10.25 G/m. With a relaxation delay of 1.26 seconds (five times the longest $T_1$ component of the samples, a 90° RF pulse being employed), the measurement time was 10.83 minutes for 8 scans.

In the second set of 1-D experiments, the centric scan 1-D FID-SPI pulse sequence of FIG. 3, was employed. By knowing the $T_1$ components 252 ms and 36 ms of Berea sandstone and setting the repetition time TR=10 ms, the RF flip angle in a Centric scan FID-SPI was chosen to be $\alpha_0$=4.5°, to minimize the $T_1$ blurring and generate an accurate spin-density map. The encoding time was 250 μs, the highest magnetic field gradient was 10.25 G/m and the relaxation delay 1.26 seconds. A total of 600 profiles, separated by τ of 8 μs, were acquired in 11.65 minutes by averaging 1000 scans. A relatively wide filter width of 125 kHz was employed in both 1-D experiments described above, in order to take advantage of a short filter deadtime, namely 19.2 μs. Centric scan 2-D FID-SPI experiments were undertaken to explore higher dimensionality imaging. The heterogeneous Locharbriggs sample (Centre for Materials Science and Engineering, University of Edinburgh) had a diameter of 37 mm and a length of 39 mm. It was a fine-to-medium grained, red-brown quartz sandstone with a bedding plane structure. For the water-saturated Locharbriggs sandstone, the bulk $T_1$ measurement gave 201.5 ms (74%) and 18.2 ms (26%), when fit to a bi-exponential recovery model. The bulk $T_2^*$ from a single exponential bulk FID for the same sample was 1470 μs. The local image intensity was calibrated with the external reference, simulating 40% porosity, employed in the 1-D FID-SPI experiments. With a repetition time TR of 10.1 ms, the RF flip angle in a centric scan FID-SPI was chosen to be $\alpha_0=4.5°$ to minimize image blurring. The encoding time $t_p$ was 250 μs, and the first profile was acquired 480 μs after the RF pulse. 50 images, separated by τ of 32 μs, were acquired in 10.5 min by averaging 32 scans. The receiver filter width was 31.25 kHz.

The last set of experiments was undertaken employing centric scan 3-D FID-SPI. The sample consisted of a whole walnut immersed in honey contained in 38.10-mm inner diameter polycarbonate cylinder; the height of the honey column was 39.25 mm (including the meniscus). The bulk relaxation times were measured before immersion. For the walnut, the bulk $T_1$ measurement gave 140.2 ms (72%) and 21.1 ms (28%), when fit to a bi-exponential recovery model. The bulk $T_2^*$ from a single exponential fit for the same sample was 6.6 ms. For honey, the bulk $T_1$ measurement gave 4.2 ms, when fit to a single exponential recovery model and the bulk $T_2^*$ from a single exponential fit for the same sample was 1.1 ms. With a repetition time TR=10.1 ms, the RF flip angle in a centric scan FID-SPI was chosen to be $\alpha_0=9°$. The encoding time $t_p$ was 250 μs, and the first image was acquired 532 μs after the RF pulse. A total of 14 profiles, separated by a τ of 32 μs, were acquired in 67 min by averaging 6 scans. A receiver filter width of 31.25 kHz was employed.

Figure 4:
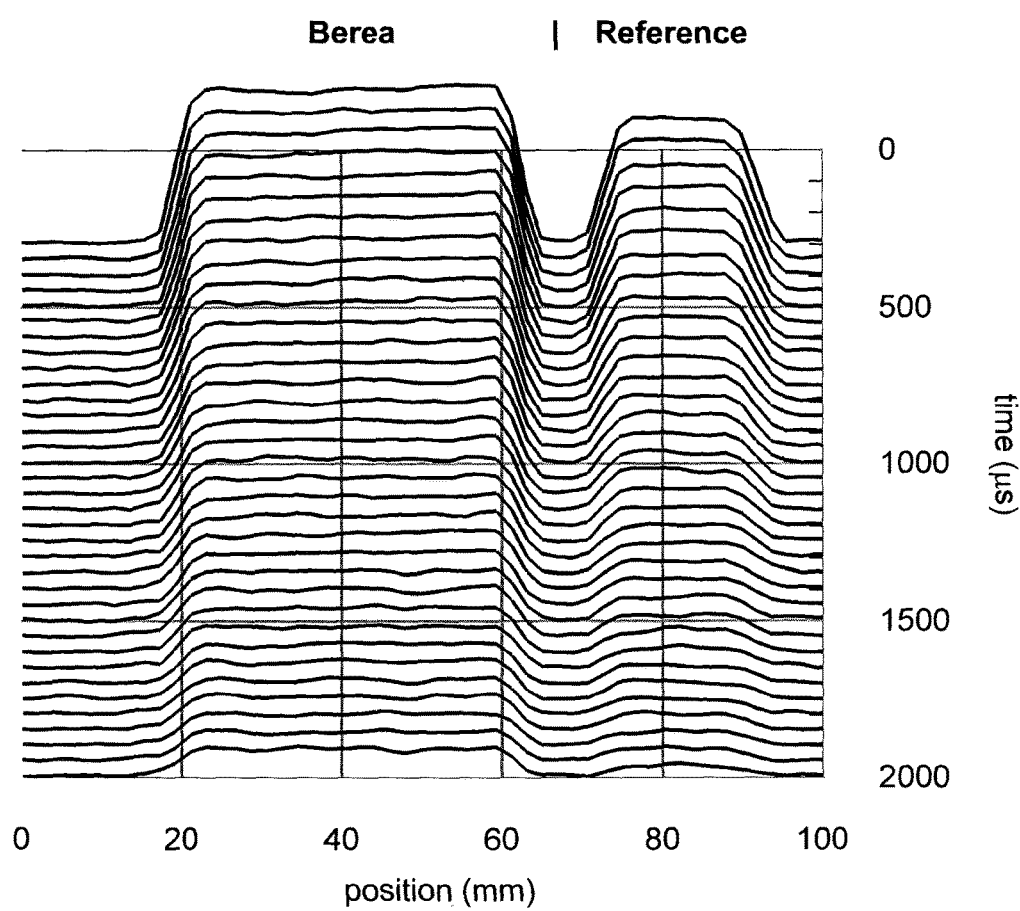
FIG. 4 are depictions of experimental profiles of a brine-saturated Berea core plug and a reference.

The ability of the sequences of the present invention to measure spatially resolved $T_2^*$s and to provide data for calculating fluid content 1-D and 2-D images for realistic rock samples was tested. A brine-saturated Berea sandstone core plug and a solution reference were measured simultaneously. In FIG. 4, axial profiles acquired with the FID-SPI sequence depict experimental profiles of a brine-saturated Berea core plug and a reference. All FID points and related profiles have identical fields of view (checked by projecting all the profiles into the time zero plane).

In fluid saturated sedimentary rocks a single exponential $T_2^*$ decay is commonly observed, which suggests that spin density imaging can be reliably obtained by the presented FID-SPI imaging technique, following pixel resolved fitting of the image series. Profile fitting, employing a monoexponential decay function naturally provides a pixel resolved $T_2^*$, i.e. a 1-D $T_2^*$ map and the local spin density from the extrapolation of the decay curves to zero encoding time (see FIG. 5). FIG. 6 displays the mono-exponential fitting curves for the central pixels of each of the profiles of the Berea sandstone core plug and the reference.

Figure 5:
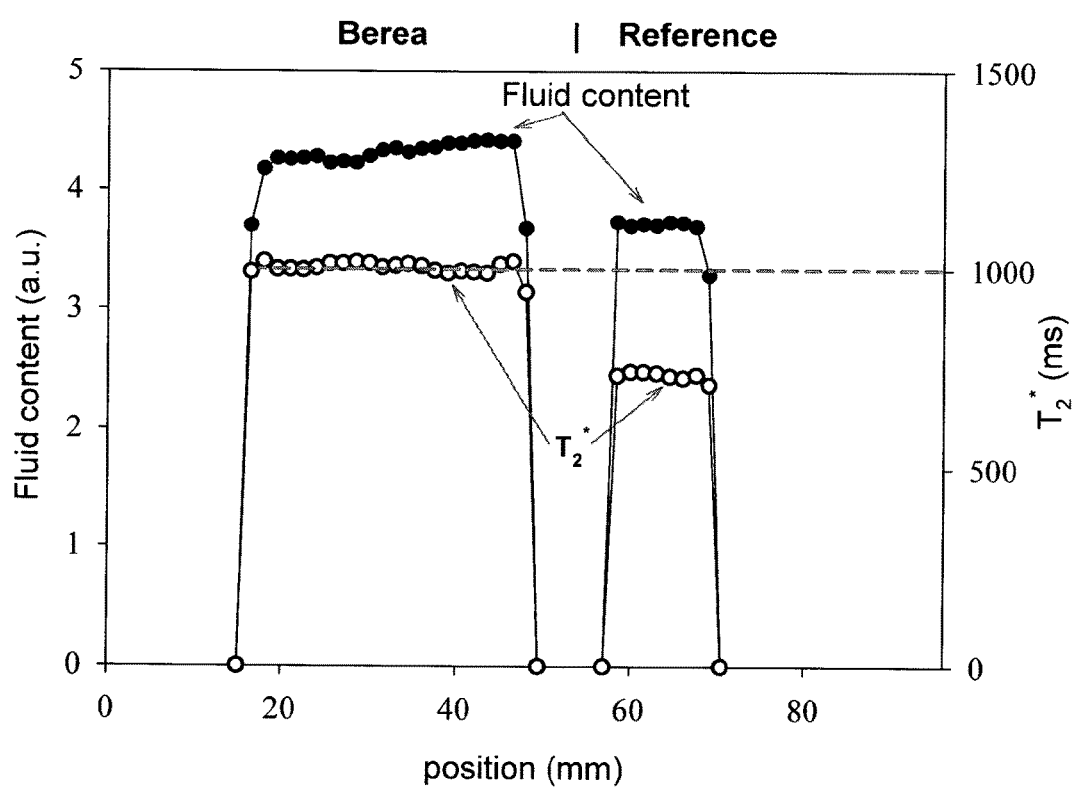
FIG. 5 is an axial spin-density map (solid circles) for the brine-saturated Berea sandstone core plug and the reference of FIG. 4 and the derived $T_2^*$ maps (open circles)
Figure 6:
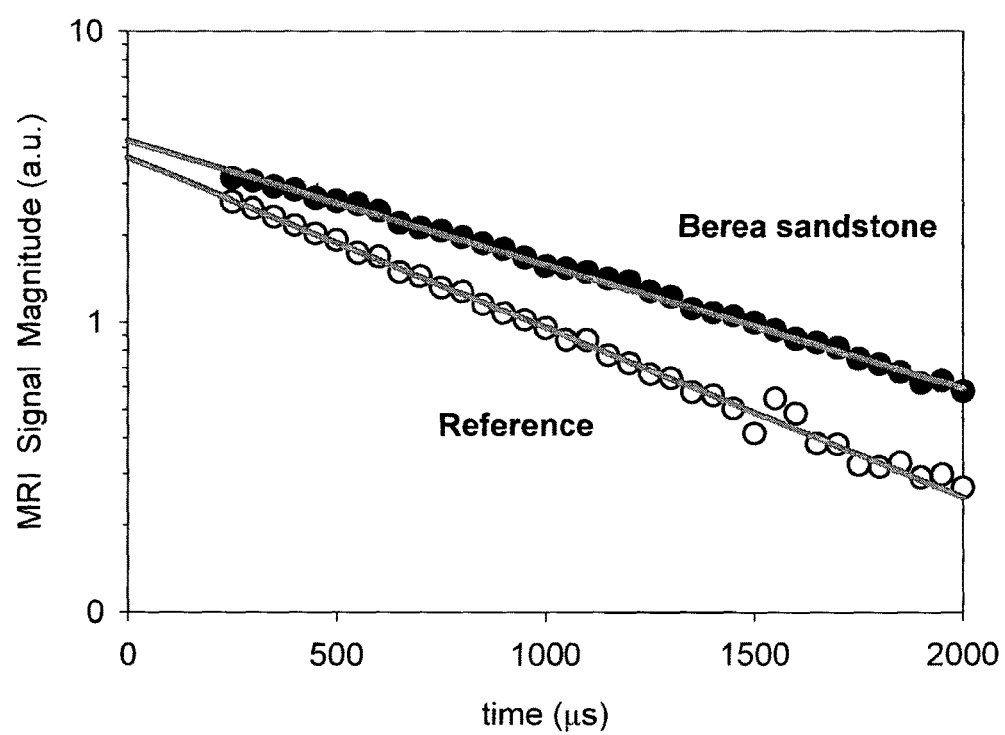
FIG. 6 are Semilog plots of signal decay for the central pixel of each of the profiles of brine-saturated Berea sandstone (solid circles) and the reference (open circles) of FIG. 4.

FIG. 5 depicts an axial spin-density map (solid circles) for the brine-saturated Berea sandstone core plug and the reference and the derived $T_2^*$ maps (open circles). Uncertainty in the data points is determined through data fitting. Uncertainty in the $T_2^*$ and the fluid content maps is generally half the data point size. All FID points and related profiles have identical fields of view (checked by projecting all the profiles into the time zero plane).

FIG. 6 depicts semilog plots of signal decay for the central pixel of each of the profiles of brine-saturated Berea sandstone (solid circles) and the reference (open circles). The $T_2^*$ decay is single exponential for each sample. The solid lines represent the corresponding monoexponential fitting curves. The derived amplitude of the profiles for these two central pixels were obtained by the extrapolation of the decay curve to zero time. The effective spin-spin relaxation times are 1,020 μs for Berea and 740 μs for the reference sample.

The pixel average $T_2^*$, calculated from the $T_2^*$ map of the homogeneous Berea was 1010±10 μs (see FIG. 5). The bulk $T_2^*$ from a single exponential fit for the same sample was 995±1 μs. Uncertainty in the data points was determined by the fitting. The quality of data is such that more complicated fitting is possible, if required. The $T_2^*$ fitting with multiple FID points yields a reliable spin density estimate, especially when $t_p \ll T_2^*$.

Referring again to FIG. 6, calculating the ratio of the mean amplitudes from the back-extrapolated profiles of the Berea sandstone and the 40%-porosity reference, and considering geometrical corrections (the ratio of the diameters of the core plug and the reference container is 1.5), the porosity of the Berea sandstone core was found to be 20.7±0.5%. This is in close agreement with the known gravimetric result of 21.0±0.1%.

All profiles in FIG. 4 have identical fields of view. This was confirmed by projecting all the profiles in the time zero plane. Identical fields of view means that all FID points have identical spatial encoding and the phase encode gradient is truly off after 250 μs. The phase encode gradients employed had a total duration of 250 μs and a 10-90% rise time of 75 μs. The performance of the resulting gradient waveform was verified by direct measurement with the magnetic field gradient waveform monitor method [15].

By decreasing the filter width from 125 kHz to 31.25 kHz in an additional 1-D sequential FID-SPI measurement, a significant increase in the SNR was observed, close to the theoretical factor of 2. The filter deadtime however increased to 456 μs. The trade-off between a relatively narrow filter width and a relatively long filter deadtime is specific to the MRI system employed. Either the sequential FID embodiment or the Centric scan FID embodiment can be employed for the fluid distribution measurements in a porous media, provided the small flip angle for the latter is determined based on an accuracy threshold [7], [11], and on the sample components. The sensitivity of the first profile acquired with the sequential FID and calculated as SNR/$\sqrt{t_{acq}}$, where SNR is the signal-to-noise ratio and $t_{acq}$ is the measurement time, was 32.8. The sensitivity of the first profile acquired with the Centric scan FID was 29.6.

The FID based MRI methods according to the present invention permit faster and more accurate spin-density mapping by acquiring hundreds of FID points and images to fit, in comparison with the earlier SPRITE mapping technique [2], where one would acquire 8 to 16 FID points and images, each requiring a separate SPRITE experiment.

By implementing a centric scan 2-D FID-SPI pulse sequence and running the corresponding experiment on a heterogeneous sample, the ability of the sequence to measure spatially resolved 2-D $T_2^*$ maps and to provide data for calculating fluid content 2-D images for a realistic rock sample was tested.

The centric scan 3-D FID-SPI pulse sequence was implemented and tested to prove its ability to acquire a series of 3-D $T_2^*$-weighted images of a complex sample. Both FID-SPI methods according to embodiments of the present invention, and prior art SPRITE techniques, are capable of generating reliable spin density maps of porous media, based on $T_2^*$ mapping measurements. The circumstances under which these measurements are performed reveal the advantage of choosing one method over the other. Assuming the minimum encoding time $t_p$ is always selected, there are three experimental regimes for quantitative density imaging [17]:

(1) when $t_p \ll T_2^*$ the observed signal is proportional to magnetization or proton density;

(2) when $t_p \approx T_2^*$, the observed signal is proportional to magnetization or proton density, if $T_2^*$ is invariant throughout the sample;

(3) if $T_2^*$ varies within the sample, with condition (1) not fulfilled, one must vary $t_p$ and perform $T_2^*$ mapping to determine magnetization or proton density.

FID-SPI imaging methods according to embodiments of the present invention are advantageous especially for case (3), since it permits faster and more accurate spin-density mapping by acquiring tens and hundreds of FID points and images to fit, in comparison with SPRITE, which requires a separate experiment for each acquired FID point and image [2].

In certain embodiments of the present invention, when applying a phase-encode magnetic field gradient pulse to the static field thereby providing spatial encoding, the duration of the phase-encode magnetic field gradient pulse should be as short as possible consistent with the functional limitations of the MRI hardware used to apply the phase-encode magnetic field gradient pulse and be consistent with a high quality phase-encode magnetic field gradient pulse. A high quality phase-encode magnetic field gradient pulse is one that is well-controlled. A well-controlled phase-encode magnetic field gradient pulse is one in which images generated from individual FID dwell times during induction decay have a consistent FOV. The durations in certain of the above examples is 250 μs. However, in certain embodiments of the present invention, the duration may be more than or less than 250 μs depending upon the MRI hardware used. In other embodiments, the duration may be 200 μs. In still further embodiments, the duration may be 175 μs. In still further embodiments, the duration may be 150 μs. In still further embodiments, the duration may be 100 μs. In still further embodiments, the duration may be between about 150 μs and about 250 μs.

Optimized Magnetic Field Gradient Waveform

Fast-switching magnetic field gradients (to assure a short encoding time) and magnetic field gradients approximately zero during the acquisition (such that subsequent FID point images have identical fields of view) are of great importance for FID-SPI methods according to embodiments of the present invention.

These experiments employed a recently developed impulse response based gradient pre-equalization method [14] in lieu of conventional pre-emphasis techniques such that optimal gradient waveforms are utilized. The magnetic field gradient waveform monitoring technique [15] directly measures the temporal evolution of the magnetic field gradient from a step-like input function and extracts the system impulse response. The impulse response is used to determine a pre-equalized (optimized) input waveform that provides a desired gradient response in the sample space.

Figure 7:
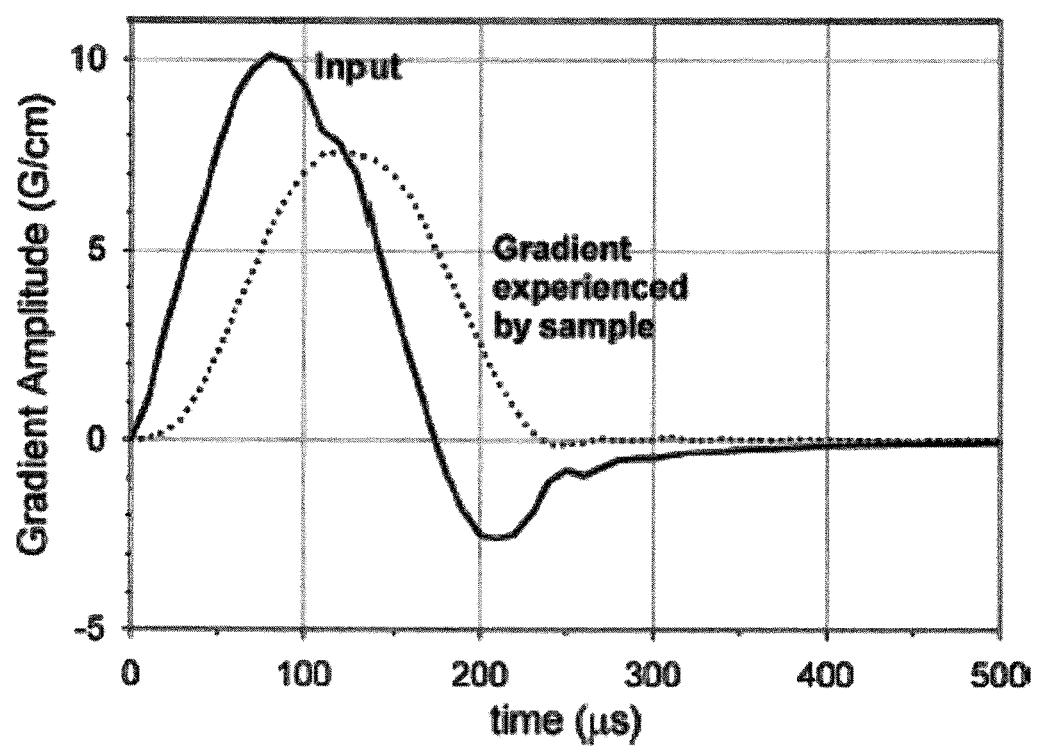
FIG. 7 is a plot of an output gradient waveform and a pre-equalized gradient waveform.

For the Y gradient coil employed in the presented experiments, the pre-equalized waveform with a duration of 8 ms, and the waveform experienced by the sample, are shown in FIG. 7. The pre-equalized waveform has a quasi-trapezoidal shape such that the gradient amplifier slew rate and bandwidth limitations (25 kHz) are not exceeded.

If the gradient area is different between FID points, we will have resulting images with different fields of view. An identical field of view (FOV) for successive FID point images, or an identical FOV between the first and last FID point images means any gradient evolution between these FID points must be below a critical threshold. One may estimate this maximum gradient area between any two FID points as an instantaneous gradient amplitude midway between the FID points, if we assume that any residual magnetic field gradient changes linearly during FID point detection. The 1-D measurements (FIG. 4) showed that the field of views for all profiles acquired after an encoding time of 250 μs are identical, which is to say any FOV differences are less than one pixel or 1.5 mm.

The maximum possible gradient error was calculated based on gradient area accumulated during the acquisition of the first two FID point profiles. Error which would lead to a variation in the FOV of less than one pixel means a maximum residual gradient of less than 3.8%. With a maximum gradient of 7.6 G/cm, this means an instantaneous gradient error between the first two FID points detected of less than 0.29 G/cm. The same calculation was undertaken for the first and the eleventh FID points. These two data points differ by 500 μs. The maximum possible gradient error which would lead to a FOV difference of one pixel is 0.48%. The maximum gradient error is thus 0.036 G/cm for the strongest phase encode gradient (7.6 G/cm), at the midpoint between the first and the eleventh FID points. Once again, this calculation assures a residual magnetic field gradient that is changing linearly between the FID points. The overall analysis assumes linear time invariant gradient waveforms as in [14]. The FOV change analysis is conceptually similar to magnetic field gradient waveform measurements reported in [16].

While the present invention has been described above in terms of specific embodiments, it is to be understood that the invention is not limited to these disclosed embodiments. Many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

REFERENCES

[1] Q. Chen, A. E. Marble, B. G. Colpitts and B. J. Balcom, The internal magnetic field distribution, and single exponential magnetic resonance free induction decay in rocks, J. Magn. Reson. 175 (2005) 300-308.

[2] F. Marica, Q. Chen, A. Hamilton, C. Hall, T. Al and B. J. Balcom, Spatially Resolved Measurement of Rock Core Porosity, J. Magn. Reson. 178 (2006) 136-141.

[3] B. J. Balcom, J. C. Barrita, C. Choi, S. D. Beyea, D. J. Goodyear and T. W. Bremner, Single-point magnetic resonance imaging (MRI) of cement based materials, Materials and Structures 36 (2003) 166-182.

[4] R. L. Kleinberg, W. E. Kenyon and P. P. Mitra, Mechanism of NMR relaxation of fluids in rock, J. Magn. Reson. A108 (1994) 206-214.

[5] B. J. Balcom, R. P. MacGregor, S. D. Beyea, D. P. Green, R. L. Armstrong and T. W. Bremner, Single Point Ramped Imaging with $T_1$ Enhancement (SPRITE), J. Magn. Reson. A123 (1996) 131-134.

[6] S. Gravina and D. G. Cory, Sensitivity and resolution of constant-time imaging, J. Magn. Reson. B104 (1994) 53-61.

[7] M. Halse, J. Rioux, S. Romanzetti, J. Kaffanke, B. MacMillan, I. Mastikhin, N. J. Shah, E. Aubanel and B. J. Balcom, Centric Scan SPRITE Magnetic Resonance Imaging: Optimization of SNR, resolution and relaxation time mapping, J. Magn. Reson. 169 (2004) 102-117.

[8] Z. H. Cho and Y. M. Ro, Multipoint K-space point mapping (KPM) technique for NMR microscopy, Magnetic Resonance in Medicine 32(2) (1994) 258-262.

[9] S. Emid and J. Creyghton, High resolution NMR imaging in solids, Physica 128B (1985) 81-83.

[10] S. Choi, X.-W. Tang and D. G. Cory, Constant time imaging approaches to NMR microscopy, International Journal of Imaging Systems and Technology 8(3) (1997) 263-276.

[11] I. V. Mastikhin, H. Mullally, B. MacMillan and B. J. Balcom, Water content profiles with a 1D centric SPRITE acquisition, J. Magn. Reson. 156 (2002) 122-130.

[12] M. Halse, D. J. Goodyear, B. MacMillan, P. Szomolanyi, D. Matheson and B. J. Balcom, Centric scan SPRITE magnetic resonance imaging, J. Magn. Reson. 165 (2003) 219-229.

[13] K. Deka, M. B. MacMillan, A. V. Ouriadov, I. V. Mastikhin, J. J. Young, P. M. Glover, G. R. Ziegler and B. J. Balcom, Quantitative density profiling with pure phase encoding, J. Magn. Reson. 178 (2006) 25-32.

[14] F. G. Goora, B. Colpitts and B. J. Balcom, Arbitrary Magnetic Field Gradient Waveform Correction using an Impulse Response Based Pre-Equalization Technique, J. Magn. Reson. 2013 (submitted).

[15] H. Han, R. P. MacGregor and B. J. Balcom, Pure Phase Encode Magnetic Field Gradient Monitor, J. Magn. Reson. 201 (2009) 212-217.

[16] B. J. Balcom, M. Bogdan, R. L. Armstrong, Single point imaging of gradient rise, stabilization, and decay, J. Magn. Reson. A 118 (1996) 122-125.

[17] C. E. Muir, B. J. Balcom, Pure Phase Encode Magnetic Resonance Imaging of Fluids in Porous Media, in: G. Webb (Ed.), Annual Reports on NMR Spectroscopy, vol. 77, Academic Press, Burlington, 2012, pp. 81-113.

We claim:

1. A method of MRI comprising:
   providing a sample space,
   providing a sample in the sample space, wherein the sample is porous media wherein the porous media comprises a solid matrix with pores containing a fluid of interest,
   applying a static magnetic field to the sample space,
   applying an RF pulse to the sample space,
   applying a phase-encode magnetic field gradient pulse to the static field thereby providing spatial encoding,
   measuring a FID signal of the sample space after the RF and magnetic field gradient pulses have ceased,
   repeating the steps of: applying an RF pulse, applying a phase-encode magnetic field gradient pulse and measuring a FID signal of the sample, wherein the step of applying a phase-encode magnetic field gradient pulse, when repeated, further comprises incrementally increasing or decreasing the phase-encode magnetic field gradient pulse relative to the last applied phase-encode magnetic field gradient pulse, and
   deriving an image of the sample from the FID signal measurements comprising applying a Fourier transform to generate a plurality of images, one image at each dwell time on the FID,
   wherein the plurality of images are used to generate an image of proton density comprising fitting a specified image pixel as a function of dwell time to yield a local value of a time constant describing the local FID decay.

2. The method of claim 1, wherein each RF pulse is a 90 degree pulse or a low flip angle RF pulse.

3. The method of claim 2, further comprising measuring the FID signals at a series of times separated by a dwell time.

4. The method of claim 3, wherein the repeated steps are repeated a sufficient number of times in order to derive an image of interest of the sample.

5. The method of claim 1, further comprising providing simultaneously two orthogonal magnetic field gradient pulses and wherein the image derived from the sample is a 2-D image.

6. The method of claim 1, further comprising providing simultaneously three orthogonal magnetic field gradient pulses and wherein the plurality of images derived from the sample is a 3-D image.

7. The method of claim 1, wherein the magnetic field gradient pulses have durations which are as short as possible such that the plurality of images have consistent FOVs.

8. The method of claim 7, wherein the durations of the magnetic field gradient pulses is less than about 250 μs.

9. The method of claim 7, wherein the durations of the magnetic field gradient pulses is between about 100 μs and about 250 μs.

10. The method of claim 1, wherein the time constant is $T_2^*$.

11. The method of claim 1, wherein the zero time intercept is proportional to fluid content in a porous media.

12. The method of claim 1, wherein the time constant corresponds to a bi-exponential decay, an exponential decay, or a non-exponential decay.

* * * * *